United States Patent
Tandon et al.

(10) Patent No.: US 11,261,465 B2
(45) Date of Patent: Mar. 1, 2022

(54) METHOD AND SYSTEM FOR INCORPORATION OF BIOMOLECULES INTO VESICLES, CELLS, AND MICELLES USING ELECTROACTIVE POROUS DEVICE MEMBRANE

(71) Applicant: The Charles Stark Draper Laboratory, Inc., Cambridge, MA (US)

(72) Inventors: Vishal Tandon, Roxbury Crossing, MA (US); Daniel K. Freeman, Cambridge, MA (US); Jonathan R. Coppeta, Windham, NH (US); Jeffrey T. Borenstein, Newton, MA (US); Jenna L. Balestrini, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 453 days.

(21) Appl. No.: 16/026,709

(22) Filed: Jul. 3, 2018

(65) Prior Publication Data
US 2019/0010516 A1 Jan. 10, 2019

Related U.S. Application Data

(60) Provisional application No. 62/528,589, filed on Jul. 5, 2017.

(51) Int. Cl.
*C12N 15/87* (2006.01)
*C12M 1/42* (2006.01)
*C12N 13/00* (2006.01)

(52) U.S. Cl.
CPC .............. *C12N 15/87* (2013.01); *C12M 1/42* (2013.01); *C12N 13/00* (2013.01)

(58) Field of Classification Search
None
See application file for complete search history.

(56) References Cited

U.S. PATENT DOCUMENTS

2012/0322097 A1 12/2012 Charest et al.
2018/0179485 A1 6/2018 Borenstein et al.

FOREIGN PATENT DOCUMENTS

WO WO 2006/112870 10/2006

OTHER PUBLICATIONS

Mir, "Electroporation-Based Gene Therapy: Recent Evolution in the Mechanism Description and Technology Developments" 1121 Methods in Molecular Biology 3-23 (Year: 2014).*

Adamo, A., et al., "Flow-through comb electroporation device for delivery of macromolecules," Anal. Chem. 85 (3): 1637-1641 (2013).
Chang, L., et al., "Dielectrophoresis-assisted 3D nanoelectroporation for non-viral cell transfection in adoptive immunotherapy," Lab Chip, 15 (15): 3147-3153 (2015).
Chang, L., et al., "Micro-/Nano-scale Electroporation," Lab Chip, 16: 4047-4062 (2016).
Dai, J., et al., "Electrokinetic Trapping and Concentration Enrichment of DNA in a Microfluidic Channel," J. Am. Chem. Soc. 125: 13026-13027 (2003).
Geng, T., et al., "Microfluidic electroporation for cellular analysis and delivery," Lab Chip, 13: 3803-3821 (2013).
Helander, I.M., et al., "Polyethyleneimine is an effective permeabilizer of gram-negative bacteria," Microbiology, 143: 3193-3199 (1997).
Kirby, B. J., et al., "Zeta potential of microfluidic substrates: 2. Data for polymers," Electrophoresis, 25: 203-213 (2004).
Lin, Y., et al., "Simulation and experimental demonstration of the electric field assisted electroporation microchip for in vitro gene delivery enhancement," Lab Chip, 4(2): 104-108 (2004).
Tandon, V., et al., "Zeta potential and electroosmotic mobility in microfluidic devices fabricated from hydrophobic polymers: 1. The origins of charge," Electrophoresis, 29 (5): 1092-1101 (2008).
Zhu, T., et al., "Electroporation based on hydrodynamic focusing of microfluidics with low dc voltage," Biomed. Microdevices. 12(1): 35-40 (2010).
Chang, L., et al., "3D Nanochannel Electroporation for High-Throughput Cell Transfection with High Uniformity and Dosage Control," Nanoscale England, 8(1): 243-252 (2016).
Chang, L., et al., "Controllable Large-Scale Transfection of Primary Mammalian Cardiomyocytes on a Nanochannel Array Platform," Small, 12(43): 5971-5980 (2016).
Ishibashi, T., et al., "A Pourous Membrane-Based Culture Substrate for Localized in situ Electroporation of Adherent Mammalian Cells," Sensors and Actuators B, 128(1): 5-11 (2007).
International Search Report and Written Opinion of the International Searching Authority, dated Oct. 15, 2018, from International Application No. PCT/US2018/040742, filed on Jul. 3, 2018. 15 pages.
International Preliminary Report on Patentability dated Jan. 16, 2020, from International Application No. PCT/US2018/040742, filed on Jul. 3, 2018. 8 pages.

* cited by examiner

*Primary Examiner* — Nancy J Leith
(74) *Attorney, Agent, or Firm* — HoustonHogle LLP (57) ABSTRACT

A method and system of delivering a charged cargo, such as a biomolecule, to a target structure, such as cells, exosomes, other vesicles or micelles, using an electroactive porous membrane. This method comprises contacting an electroactive porous membrane with a fluid flow toward the membrane. The fluid contains charged biomolecules and the membrane and biomolecules are oppositely charged so that the biomolecules in the fluid are trapped on the membrane as the fluid flows through the pores of the membrane. Acceptor cells of interest are pinned to the membrane by the flow of the fluid, thereby aggregating the cells onto the membrane in close proximity to the trapped biomolecules. Finally, the acceptor cells are permeabilized.

9 Claims, 8 Drawing Sheets

METHOD AND SYSTEM FOR INCORPORATION OF BIOMOLECULES INTO VESICLES, CELLS, AND MICELLES USING ELECTROACTIVE POROUS DEVICE MEMBRANE

RELATED APPLICATIONS

This application claims the benefit under 35 USC 119(e) of U.S. Provisional Application No. 62/528,589, filed on Jul. 5, 2017, which is incorporated herein by this reference in its entirety.

BACKGROUND OF THE INVENTION

Various methods have been developed for transferring genes into cells. These include: (i) using viral vectors (such as Lentiviruses) for gene delivery, (ii) mechanical methods such as microprecipitation, microinjection, liposomes, particle bombardment, sono- or laser-induced poration, bead transfection, gene guns, and magneto-transfection, (iii) conventional, bulk electroporation systems; and (iv) chemical transfection techniques.

An example of an emerging commercial mechanical method uses cell membrane disruption to deliver a cargo into cells. It has demonstrated the ability to deliver a wide range of cargos into numerous primary cell types with minimal impact on function and viability.

Electroporation techniques include, for example, flow electroporation, pulse-controlled electroporation, and microfluidic devices with varying geometries or operating principles, such as comb electroporation, dielectrophoretically-assisted (or DEP-assisted) electroporation, and electroporation in a hydrodynamically focused stream.

Finally, some have demonstrated electrokinetic concentration of a bolus of DNA in a microfluidic channel using an embedded, porous, polytetrafluoroethylene (PTFE) device membrane.

SUMMARY OF THE INVENTION

Conventional electroporation methods rely on flooding the system with a large concentration of material to be transferred. This increases the potential for uncontrolled transport of material into and/or out of cells, resulting in a high number of vector integrations, which can lead to mutagenesis. Conventional electroporation methods also can require application of high fields that are not precisely tuned at the cellular level. Furthermore, electroporation tends to be much less effective for DNA insertion (when compared to RNA insertion), because the material must cross two phospholipid bilayer membranes (the cell membrane and the nuclear membrane).

On the other hand, it has been demonstrated that preloading and immobilization of plasmid DNA in a microfluidic system using positively charged electrodes can lead to more efficient gene delivery. However, previous approaches have required adherent cells (cells grown in a monolayer, for instance, on an artificial surface). This restriction limits a more generalized application of this approach.

In fact, most existing electroporation systems do not offer any means for controlled cargo delivery, and therefore produce cells with uncontrolled numbers of gene integrations or low nuclear delivery efficiency. Moreover, with these systems, there is typically a trade-off between efficient gene transfer and cellular damage; thus, there is a penalty associated with trying to increase efficiency. Patterning DNA on the surface of a device membrane offers the potential for controlled gene delivery. There is one example of patterned electrodes being used to hold plasmid DNA on a surface for electroporation. However, only adherent cells will stick to it without additional modifications.

The present system and method concern the electrostatically trapping of a cargo, typically a charged material such as plasmids, DNA or RNA, on a charged surface that is permeable to fluid flow but impermeable to cells. Generally, it concerns a method and system for incorporation of biomolecules into target structures (e.g., vesicles, cells, micelles) using an electroactive porous device membrane. The fluid flow, typically in conjunction with the pore configuration of the device membrane, enables the pinning of target structures onto the surface of the device membrane. This technology, therefore, can be used with non-adherent cells, such as T-cells hematopoietic stem cells (HSCs), or unattached free-floating adherent cells such as mesenchymal stem cells (MSCs), neurons, epithelial cells, endothelial cells and others.

The system offers the potential for relatively well-controlled gene or vector delivery by localizing the target structures, such as cells or exosomes, and cargo, such as plasmids, together on a device membrane. This system would improve control over the number of gene integrations per cell, for example, during an electroporation process. This system would also enable the control and loading of materials smaller than cells, such as exosomes, and loading them with a variety of materials. Furthermore, the use of a device membrane that is porous to fluid flow allows this system to be used with a variety of cell types or biological materials. The approach can be facilitated because of the ability to entrain cells through the use of transmembrane pressure.

This system is primarily intended to be used as part of a system for modifying cells or other target structures using genetic material for use in cell therapy. Target structures loaded with cargo can be used for treatment of diseases such as heart disease, cancer, lung disease, liver disease, multiple sclerosis, hemophilia, Parkinson's, glaucoma, kidney disease, cystic fibrosis, stroke and graft-versus-host disease. They can also be used for the treatment of injury such as spinal cord injury, chronic wounds, or stroke or the delivery of therapeutic agents such as vaccinations, biological components, or chemokines.

Moreover, this technology can potentially be used for controlled delivery of almost any type of charged biomolecules to cells or materials such as liposomes. For example, cells could be modified for use as sensors to report biological phenomena within the body, or as living delivery systems.

The initial embodiments of the system might utilize test target structures that establish functionality, but preferred embodiments of the invention can be integrated into a full cell or exosome transfection and processing system.

The general purpose of this system and method is to reversibly concentrate, pattern, and trap the cargo, such as plasmid DNA or other electrically charged molecules, on an electroactive porous device membrane for controlled delivery of the molecules to cells, such as for genetically modifying the cells. The device membrane is intended to be integrated into a fluidic structure, such as a microfluidic device, so that cargo structures are guided to the device membrane (or specific locations on the device membrane) by a combination of fluid flow and electrokinetic and/or electrostatic forces imposed by the geometry of the fluidic structure.

Trapping and concentration of charged molecules is preferably accomplished by applying voltage to a metal or metallized polymer membrane, or by chemically modifying a polymer membrane to carry a net charge, and then transporting oppositely charged molecules toward the membrane where they become trapped.

Typically, subsequent to sequestration of the negatively charged cargo material, target structures such as cells or exosomes are entrained and directed toward the trapped molecules by flow, where they are trapped due to pore-size constraints of the device membrane. Trapped cargo can then be released by changing the magnitude or polarity of the applied voltage, or by subsequent chemical modification of the device membrane.

Specifically engineered topographic features can be imposed on the electroactive device membrane by embossing or other techniques used to form features or patterns configured for enhanced control of the distribution of cells and molecules, and/or to shape the electric field in the vicinity of the device membrane.

In order to facilitate transfer of molecules into the cells, the cells may be permeabilized by electroporation, sonoporation, or some other means. In some embodiments, permeabilization is accomplished by using the electroactive device membrane itself.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

A common technique used to temporarily permeabilize cells is electroporation. Parameters considered when developing electroporation procedures include cell properties (cell size, shape, membrane structure, surface charge, for example), the cell environment, and attributes of the applied electric field, (e.g., pulse intensity, number of pulses, pulse duration, pulse shape and/or frequency). It is generally believed that membrane permeabilization during electroporation occurs after the applied electric field induces a threshold value in the transmembrane potential or "electroporation threshold" and that, at a given applied electric field, there is a threshold for the number of pulses and pulse length, needed for successful electroporation.

The system described herein can be used to concentrate, pattern and trap one or more material(s), referred to herein as "cargo" or "payload", for controlled trans-cell-membrane delivery of the cargo to target structures, such as, for example, cells, micelles and vesicles, e.g., synthetic vesicles such as liposomes or naturally occurring cell-derived vesicles such as exosomes.

Attractive for potential uses in prognosis, therapy, or as biomarkers, exosomes, for instance, are cell-derived vesicles that are present in many if not all eukaryotic including blood, urine, as well as cell culture media. Generally, exosomes are composed of lipid bilayer membranes with multiple adhesive proteins on their surface and can include mRNA or microRNA. Known for their cell-to-cell communication characteristics, it is thought that exosomes may find applications in targeted cell therapy.

Whereas eukaryotic cells typically have a diameter within the range of from about 10 to about 100 micrometers ($\mu m$), typical exosome diameters are between 30 and 100 nanometers (nm). At such reduced dimensions, exosomes are also smaller than most prokaryotic cells (0.1-5.0 $\mu m$ in diameter).

Exosomes can be modified to carry payloads such as, for example, biomolecules, proteins, peptides, antibodies, nanoparticles, and pharmaceuticals, e.g., for therapeutic drug delivery.

As known in the art, liposomes are spherical vesicles having at least one lipid bilayer that can be used as a vehicle for administration of nutrients and pharmaceutical drugs.

In addition to membrane-bound structures such as described above, embodiments described herein can be practiced using other target structures, such as, for instance, micelles, generally defined as loosely bound aggregations of atoms, ions or molecules, forming a colloidal particle (i.e., one of a number of ultramicroscopic particles dispersed through a continuous medium). Micelles are particularly important in surface chemistry, playing an important role in the dispersion by soap solutions of organic compounds insoluble in water, for example.

The target structures can be characterized by their size. Some have a diameter that is less than or equal to about 100 nm, for instance within the range of from about 30 to about 200 nm. Others have a diameter that is within the range of from about 10 to about 100 µm. In further cases, the target structures have a diameter within the range of from about 0.1 to about 5.0 µm.

In many embodiments the target structure is a nanoparticle, i.e., a vesicle or micelle having a diameter equal or less than 100 nanometers (nm), such as, for example, within the range of from about 30 to about 100 nm. In other embodiments, the target structure is a microparticle, e.g., a cell, having a diameter greater than about 100 nm. The microparticle can have a diameter of up to 25, 50, 75, or 100 µm. T-cells, a common type of membrane bound structures for electroporation transfection, for example, range in size from about 6 µm to 12 µm.

As described herein, the present invention specifically provides a porous electroactive device membrane capable of trapping and/or holding the cargo on the device membrane in order to facilitate the delivery of cargo to the target structure of interest.

In a specific implementation, DNA is trapped on a charged surface that is porous to fluid flow. Target structures (cell, exosomes, etc.) are pinned or trapped onto the surface by fluid flow in proximity to the electrically-trapped cargo.

Other suitable cargo materials include but are not limited to small molecules, proteins, plasmids, chromosomes, RNA, e.g., mRNA, siRNA, gRNA, ssRNA, nucleic acid sequences, such as DNA, cDNA, siDNA and RNA sequences other genetic materials, oligomers, biomarkers, proteins, transposons, biomolecules, e.g., biomolecular complexes, small molecules, viral particles, therapeutic agents, and so forth.

Figure 1:
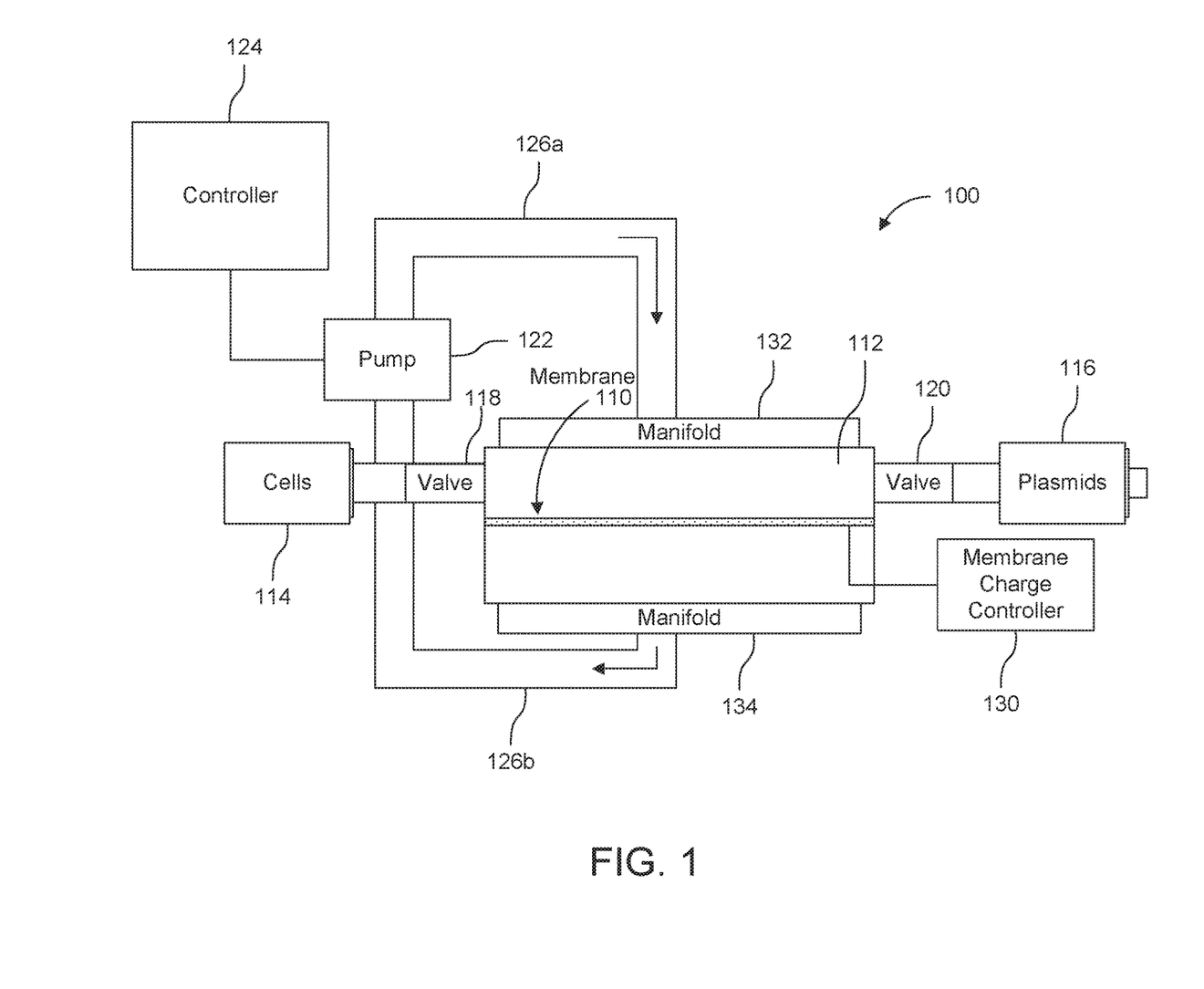
FIG. 1 is a schematic block diagram showing a system for transferring a cargo into target structures such as cells or exosomes.

FIG. 1 shows a gene transfer system 100, which has been constructed according to the principles of the present invention.

The system 100 comprises a device membrane 110 that extends across a reservoir 112. A pump 122 directs a fluid flow via delivery line 126a through the device membrane 110. The fluid returns to the pump 122 via a return line 126b. Optional flow manifolds 132 and 134 can be provided, e.g., at the top and bottom, respectively, of reservoir 112. The fluid flow can be continuous or intermittent.

Connected to the reservoir 112 is a target structure (e.g., cell or exosome) container 114 and cargo container 116. In one implementation, the cargo container 116 includes plasmids. As generally known, a plasmid is a small DNA molecule within a cell that is physically separated from a chromosomal DNA and can replicate independently. Typically encountered as small circular, double-stranded DNA molecules in bacteria (and sometimes in archea or eukaryotic cells), plasmids often carry genes that may benefit the survival of the organism, for example antibiotic resistance. While chromosomes contain all the essential genetic information for living under normal conditions, plasmids usually are very small and contain only additional genes that may be useful to the organism under certain circumstances or conditions. Artificial plasmids are widely used as vectors in molecular cloning, serving to drive the replication of recombinant DNA sequences within host organisms. In the laboratory, plasmids may be introduced into a cell via transformation.

A valve 118 connects the cell container 114 to the reservoir 112 so that the target structures can be released into the reservoir 112. In a similar way, the cargo in the plasmid container 116 is released into the reservoir 112 using a valve 120. A controller 124 controls the cell container valve 118 and the plasmid container valve 120 along with the pump 122 and a device membrane charge controller 130. Some implementations utilize micropipetters including but not limited to manual or automated fluid transfer devices capable of transporting target structures and cargo from their respective containers.

In operation, the controller 124 controls the device membrane charge controller 130 to apply a net, electrostatic charge to the device membrane 110 in the cell fluid, which is usually an aqueous solution. Then, the controller 124 controls valve 118 to release the plasmids into the cell reservoir 112. The charge is used to temporarily trap molecules of the opposite charge.

Typically, the device membrane 110 is intended to be integrated into the reservoir or receptacle 112, which is typically a microfluidic device, a cell culture plate, or a Transwell insert. The material of the device membrane 110 can be a polymer (such as polycarbonate, nylon, polyester, polyether sulfone (PES), polyvinylidene fluoride (PVDF), etc., a metal (such as titanium, gold, or silver), or a ceramic (such as silicon nitride). Composite materials comprising, for example, a substrate and possibly a conductive coating, also can be utilized. The conductive coating that is applied to the substrate can also have a dielectric coating to separate the electrostatic charge on the metal from the aqueous solution. In specific examples, the device membrane is constructed of metal or a metalized polymeric (plastic) material.

The pores may be configured to a particular target structure. In some implementations, the device membrane 110 is or includes a semipermeable membrane having pore diameters that are smaller than the diameters of the target structures (cells, other vesicles, and so forth). In other implementations, the device membrane 110 is or includes a semipermeable membrane having pore diameters smaller than the diameters of the payload structures (plasmids, mRNA, etc.). In one example, the device membrane 110 has a pore size within the range of from about 0.005 to about 5 micrometers (µm) and a thickness within the range of from about 5 to about 50 µm.

A net charge can be imposed on the device membrane 110 by several different mechanisms, depending on the membrane composition. A metal or metal-coated polymer/ceramic device membrane 110 can receive the electrostatic charge from the membrane charge controller 130, which can simply be a switched voltage source. The voltage applied to the membrane could be referenced to another conductive device membrane contained within the same aqueous solution, or the voltage could be referenced to an electrode that is not involved in trapping DNA, such as a platinum or silver wire. The voltage applied can have a value of about 100 mV to about 100 V or higher. In some cases, the vector (cargo) is electroactive (e.g. DNA) and direct contact with a charged surface above the threshold redox potential should be avoided to minimize the chances of damaging the vector. In these cases, potentials higher than the redox potential may be used by locating the charged electrode on the side of the membrane opposed to the side the DNA is trapped.

Other examples utilize a polymer membrane that naturally develops a net electrostatic charge in aqueous solution depending on the properties of the immersing liquid (pH, salt concentration, etc.). The membrane can also be modified with a chemical group (e.g. polyethylene glycol) that develops a net charge in solution. The device membrane could also be an electret (i.e., a dielectric material that has a quasi-permanent electric charge or dipole polarization), such as a polymer membrane that is corona-charged outside of solution to have a semi-permanent charge. Alternatively, layer-by-layer polyelectrolyte adsorption coatings may be used to create a fixed charge. For example, alternating layers of poly(styrene sulfonate) and polyethyleneimine can be used to create a terminal positive (polyethyleneimine) or negatively (poly(styrene sulfonate) charged surface.

For voltage-controlled device membranes, the device membrane charge can be augmented or reversed by changing the applied voltage from the membrane charge controller 130. Trapped cargo (plasmids) can then be gently released by grounding the device membrane 110 or repelled by reversing the polarity of the device membrane so that it has the same charge as the trapped molecules. This repulsion is used to drive plasmids into cells during an electroporation process. For device membranes that are chemically modified to carry a net charge in solution, release of trapped molecules is achieved by a subsequent chemical modification that cleaves, chelates, or neutralizes the surface modification.

System 100 can be used for controlled delivery of genetic cargo (e.g., plasmids, siRNA, etc.) into target structures, such as cells, exosomes, other vesicles, micelles, etc.) in an electroporation process.

Figure 2:
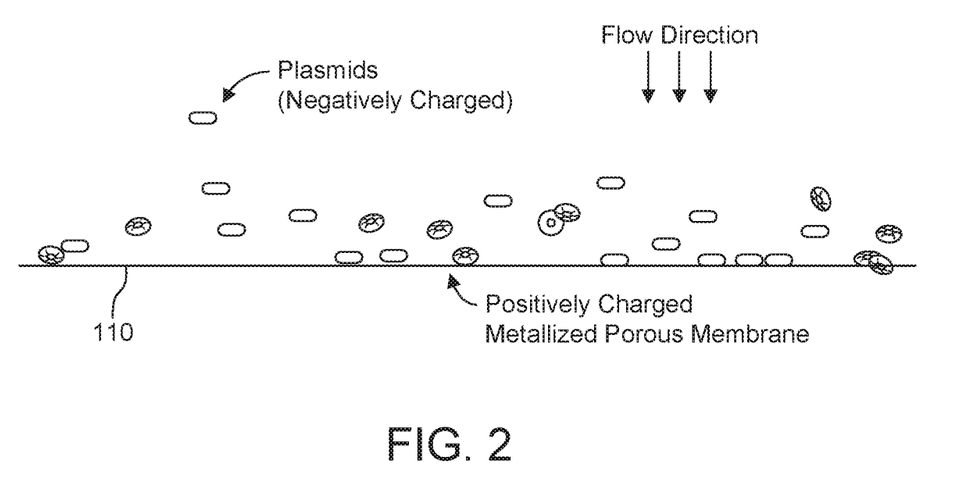
FIGS. 2, 3, 4, and 5 are schematic side views showing the positively charged metallized porous device membrane trapping cargo, e.g., plasmids, the trapped plasmids on the positively charged porous device membrane, the target structures, cells or exosomes, being pinned down to the positively charged device membrane by flow through the device membrane, and the device membrane charge being reversed to negative releasing the plasmids, respectively.

As shown in FIG. 2, the controller 124 by control of the membrane charge controller applies a positive voltage to a device membrane (e.g., made of metal or including a metal component) 110, and a negatively charged cargo, negatively charged plasmids or vector, for example, are loaded onto the device membrane 110 by flow, such as generated by pump 122 under the control of the controller 124. The plasmids or vector then become trapped. Specifically, the device membrane holds the cargo onto an oppositely charged surface that is porous to fluid flow. The combination of the charged cargo, such as plasmids, the charged membrane, and possibly the membrane pore size, prevents the cargo from simply flowing through the device membrane 110. This flow, however, enables pinning of large cells onto the surface with fluid flow, since the cells are too large to pass through the pores in the device membrane. In one embodiment, the fluid flow direction within reservoir 112 is perpendicular or substantially perpendicular to the device membrane 110. For instance, the fluid flow can be directed from delivery line 126a toward device membrane 110 using manifold 132. Manifold 132 can be configured with perforations, channels or other suitable openings for the distribution of fluid (e.g., in shower head fashion) onto the device membrane.

The fluid flow also can play a role in carrying away excess heat generated during electroporation and/or during other steps employed such as, in some embodiments, electrophoresis (the movement of charged particles in a fluid or gel under the influence of an electric field).

Figure 3:
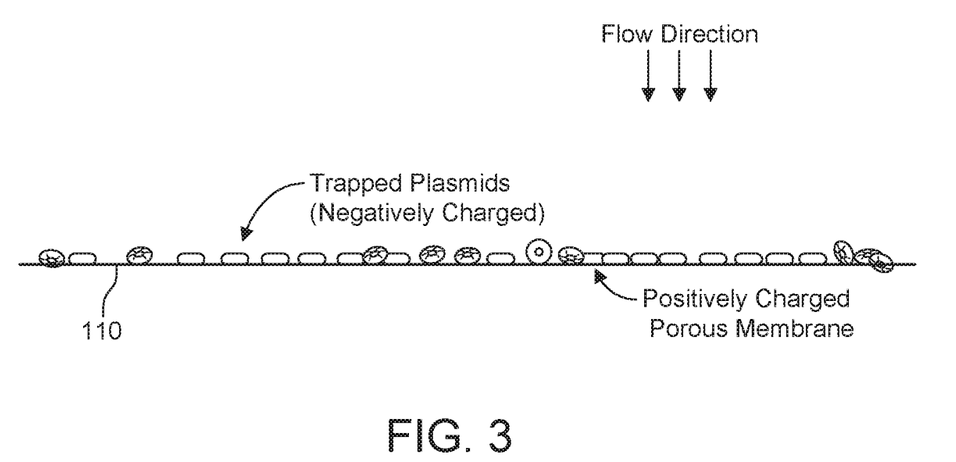

In the process described herein, electrophoretic forces can be used, alternatively or in combination with electrostatic attraction, to promote or facilitate concentrating the cargo, e.g., plasmids, at the device membrane 110, as shown in FIG. 3.

Figure 4:
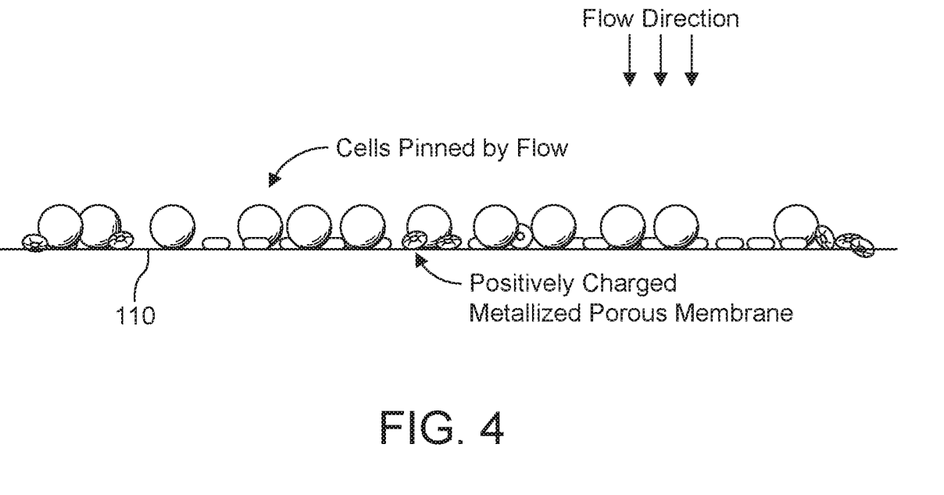

Next, the controller 124 releases the target structures from the cell container 114 by opening the cell container valve 118. The target structures, e.g., membrane-bound structures or micelles, are collected or aggregated onto the device membrane 110 by flow of the fluid in the reservoir 112 generated by operation of the pump 122, as shown in FIG. 4. If electrically charged, the transport of the target structures can be enhanced by electrophoretic forces. The target structures cannot pass through the device membrane 110 because they are larger than the pores of the device membrane.

Other sequences for the release of cargo and target structures can be employed. For instance, the cargo can be released after the target structures. Simultaneous release of both target structures and cargo also is possible. Furthermore, some embodiments employ a common container (reservoir) for holding both free floating target structures and cargo.

Regardless of the sequence in which cargo and target structures are released to reservoir 112, many embodiments are conducted by placing (positioning) the cargo at device membrane 110 before the disposition of target structures on the device membrane. Other sequences can be employed. For instance, both cargo and target structures can be driven toward the device membrane at the same time. In further implementations, target structures can be disposed on the device membrane before the cargo.

The cargo can be driven toward and held, pinned, trapped, retained, etc., at the surface of the device membrane using electrostatic forces and/or other techniques, such as, for instance, electrophoresis, a pore structure that prevents passage of the payload material, and so forth. In some cases, cargo at the surface of the device membrane is not immobilized but rather manipulated in dynamic fashion. Target structures are held, pinned, trapped, retained, etc., at the surface of the device membrane (e.g., by a membrane pore structure that prevents their passage) and can agglomerate in close proximity to the cargo.

Permeabilization of the target structures can be carried out by electroporation, sonoporation, use of the device membrane itself or other suitable techniques. In one example the device membrane 110 is electroactive. The controller then instructs the charge controller 130 to changes the charge on the device membrane, the electric field generated by the electrostatic charge on the membrane can act to permeabilize the cell lipid bilayer membranes. This creates pores in the cell membrane to allow cargo, plasmids, for instance, to enter the cells. In other examples, the membrane charge controller initiates electroporation by use of electrodes that are independent from the device membrane 110. The voltage applied to effect electroporation can be supplied in pulses. Its magnitude often is higher than that of voltages typically used to produce electrophoretic forces suitable for the transport of cargo and/or target structures toward the membrane device.

Figure 5:
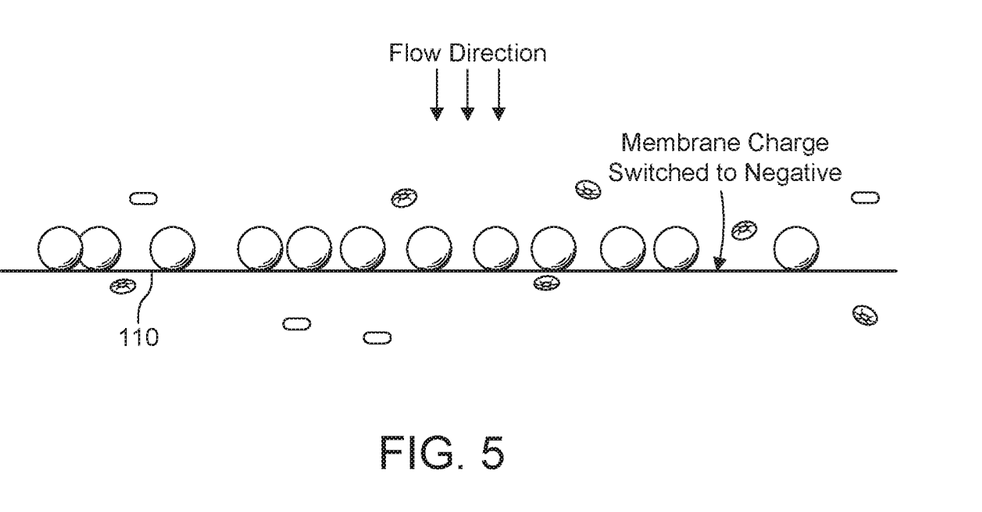

The plasmids or other cargo are then released and pushed into the cells by reversing the polarity of the voltage applied to the device membrane 110 by the membrane charge controller 130 (see FIG. 5).

The loaded target structures (cells, for example) are then removed from the system for use. Various approaches can be employed. In one example, loaded target structures are collected from device membrane 110 using a micropipette. For example, inlet and outlet microchannels can be connected to the cell-containing fluid chamber on the top side of the membrane. Flow out of the fluid chamber on the bottom side of the membrane is blocked, and flow across the top side of the membrane is used to collect cells. Alternatively, flow coming from the bottom side of the membrane can be used to aid in cell removal.

Figure 6:
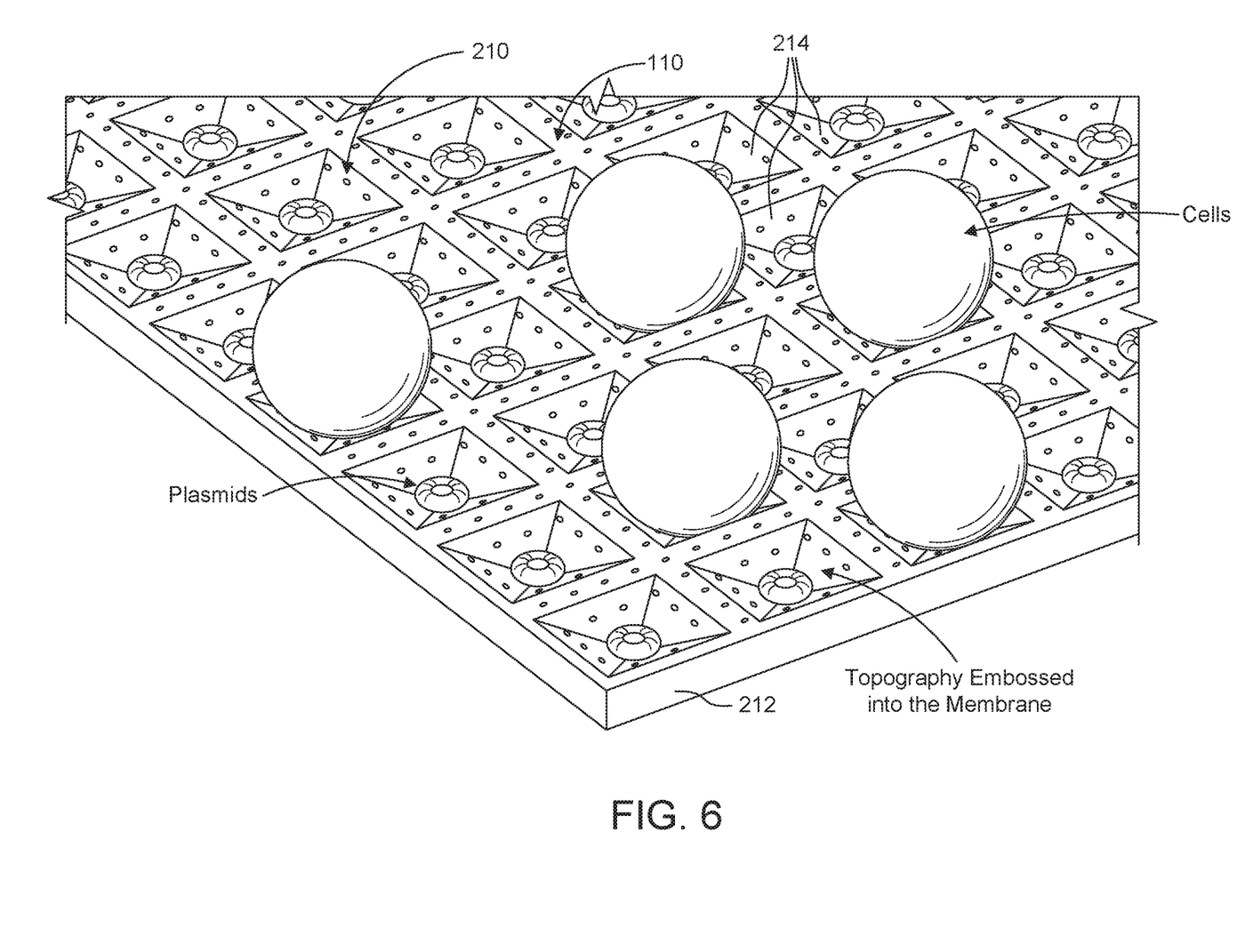
FIG. 6 is a partial top perspective view showing exemplary topographical features, embossed, e.g., into the electroactive device membrane for promoting control of the distribution of trapped cargo structures and/or target structures across the device membrane. (Note: the size of the plasmids is greatly exaggerated)

FIG. 6 shows a portion of an exemplary device membrane 110. In this example, the membrane substrate 212 is fabricated from a polymer that has been hot-embossed against a mold to impose surface features such as indentations or concavities 214. Similar indentations also can be formed in non-polymeric device membranes. In addition to embossing processes, desired patterns and features can be produced by carving, stamping, molding, laser ablation, etching (KOH etched (1 0 0) silicon or reactive ion etching, photolithography combined with etching, wire electrical discharge machining (EDM), diamond turning, etc., as known or as developed in the art.

The concavities 214 or other features (e.g., conical, pyramidal, polygonal, irregular or other types of indentations, as well as various grooves, channels, hemispherical or hemieliptical cavities, etc.) can shape the electric field in the vicinity of the device membrane 110 in order to encourage a more ordered trapping of the cargo material (e.g., plasmids) and target structures (e.g., cells) on the device membrane 110. In the embodiment of FIG. 6, both the plasmids and the target structures (cells) are larger than the membrane pores 210. In some implementations, the membrane topography, e.g., concavities 214, also provides physical barriers, in the form of lips, rims, raised boundaries, etc. that help to order cells or other target structures. In addition to, or as an alternative of concavities 214, the surface of the device membrane can be roughened, resulting in an increased surface area.

Dimensions associated with these features, concavities 214, for instance, can depend on various factors, such as, for example, the size of the target structure, the desired local magnitude of the electric field to be applied, the desired field gradients, field distribution, and so forth. The device membrane can be configured to have a uniform or regular pattern. For instance, all the features, e.g., concavities 214 can have the same dimensions and/or are formed at regular intervals on the surface of the device membrane. Other arrangements are possible.

In another implementation that aims to enhance the trapping of target structures, electrodes are patterned in a desired configuration onto the device membrane 110 and then powered by the membrane charge controller 130 to generate specific arrangements (patterns) in which target structures are loaded onto the device membrane 110.

The electroactive device membrane 110 itself can be used to apply the permeabilizing electric field to the cells. At low applied voltages (<~1V) the electric field would only penetrate approximately one Debye length (typically 1-100 nm) into the cell (or another target structure), resulting in a highly localized permeabilization. At higher voltages, the membrane-electrode pair can pass Faradaic current, resulting in penetration of the electric field throughout the fluid. On the other hand, with a membrane device that can be electrically charged to permeabilize the target structures, the requirement for a pair of electroporation electrodes, each separate from and disposed externally to the device membrane 110, can be bypassed.

The arrangements and operating principles described herein can be incorporated in a microfluidic device. One example of such a device is provided in U.S. patent application Ser. No. 15/851,393, with the title SYSTEM AND METHOD OF USING A MICROFLUIDIC ELECTROPORATION DEVICE FOR CELL TREATMENT, to Borenstein et al., filed on Dec. 21, 2017 and published on Jun. 28, 2018 as U.S. Patent Application Publication No. 2018/0179485A1, which is incorporated herein by this reference in its entirety. In one implementation, the membrane used in the microfluidic device of U.S. application Ser. No. 15/851,393 is replaced with a device membrane according to embodiments described herein.

Figure 7:
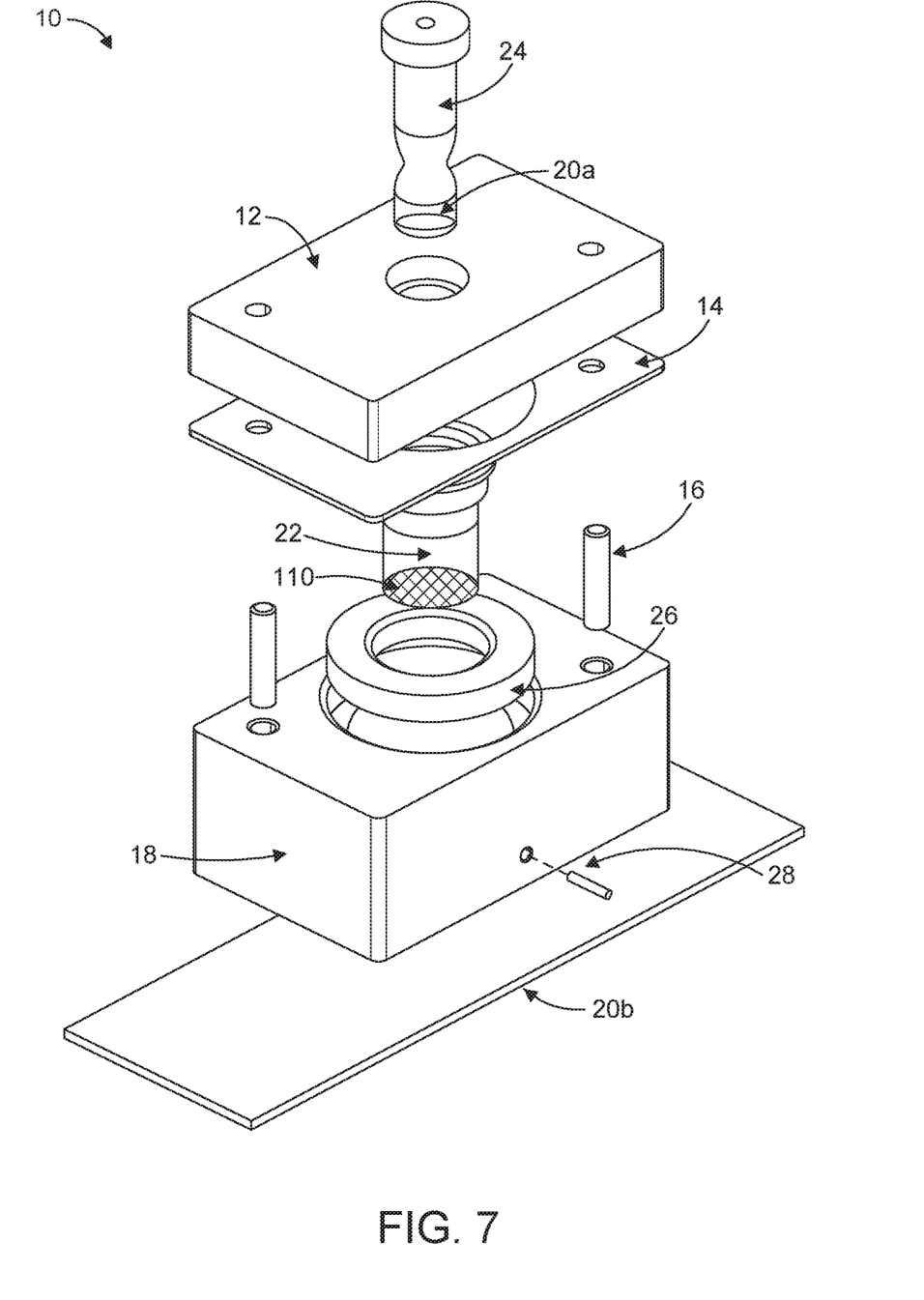
FIG. 7 is an exploded perspective scale view of a microfluidic electroporation device according to some implementations.
Figure 8:
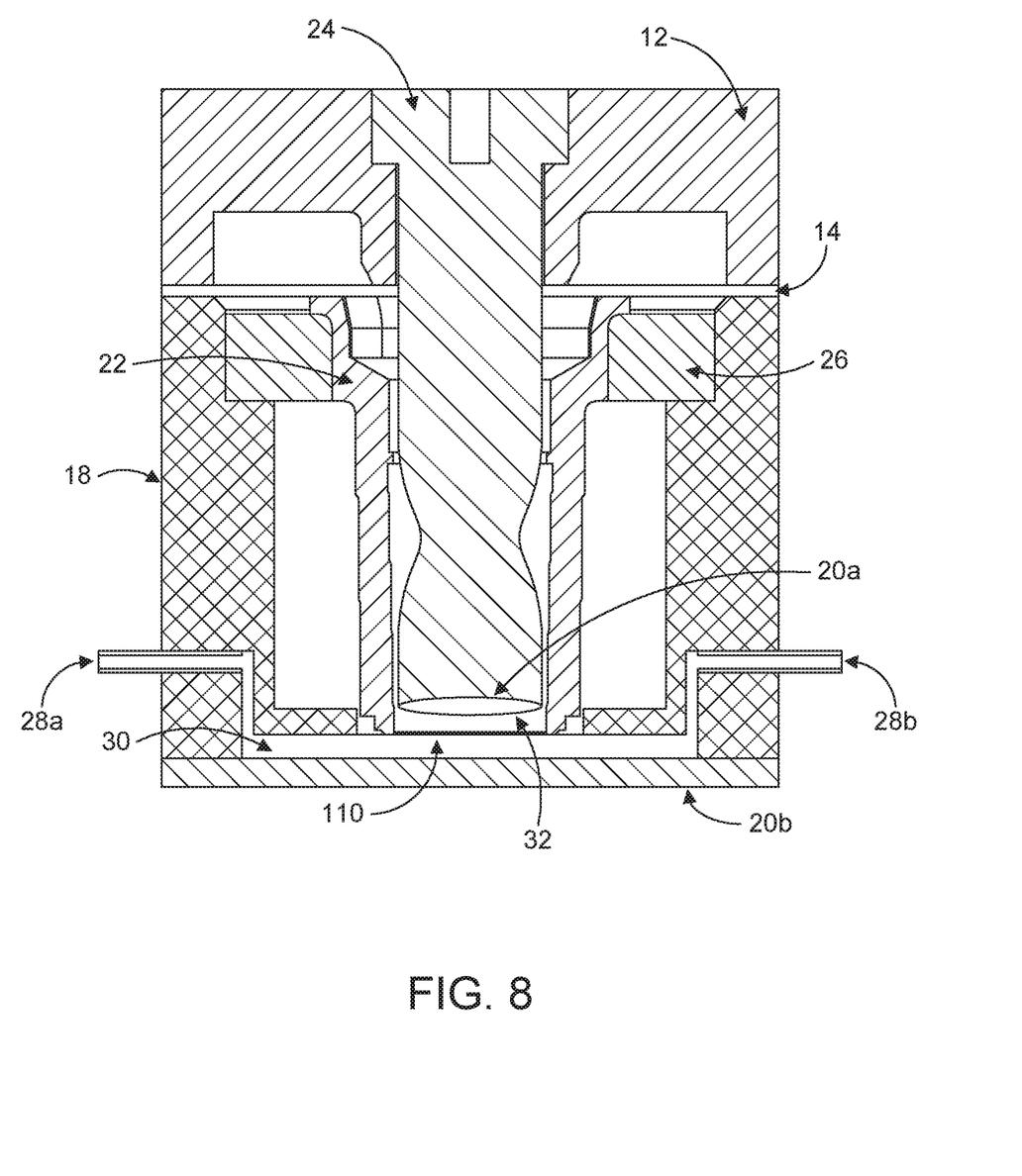
FIG. 8 is a cross-sectional scale view of an assembled microfluidic electroporation device according to some implementations.

Shown in FIGS. 7 and 8, for example, is the microfluidic electroporation device 10 which includes an upper housing 12. The upper housing 12 is mated to a shim 14 and includes one or more elements to receive the alignment structures 16. The arrangement of the elements to receive the alignment structures 16 may vary depending on the design of the microfluidic electroporation device 10 and the positioning of the alignment structures included in the base 18. The upper housing 12 is configured to receive an electrode, such as electrode 20a, introduced through the upper housing and into the fluid receptacle 22. Once the fluid receptacle 22 has been inserted into the base 18, the upper housing 12 is positioned atop the shim 14 and base 18. The target structures and cargo can be introduced through the upper housing 12 into the fluid receptacle 22 after the upper housing has been positioned atop the shim 26 and the base 18. In some implementations, the target structures and cargo are introduced into the fluid receptacle 22 before the upper housing is mated to shim 26 and the base 18.

The microfluidic electroporation device 10 can include one or more electrodes employed to provide an electrical charge to device membrane 110 and/or to conduct the electroporation operation. In the embodiment of FIGS. 7 and 8, for instance, electrodes 20a can be configured to contact and electrically charge the device membrane 110. In other approaches, electrode 20a is positioned in close proximity to the device membrane 110, to provide, together with electrode 20b, an electric field, suitable, for example, for the electrophoretic transport of cargo, or for the electroporation process.

To facilitate its insertion, the electrode 20a can be provided within the electrode insert 24, which extends through the upper housing and into the fluid receptacle 22. The shape of the electrode insert 24 can be configured to reduce the amount of fluid displaced upon its insertion in the fluid receptacle. In one example, the electrode insert has a tapered body. In other implementations the electrode insert 24 includes a coil shaped insert to further reduce fluid displacement and enhance the release of the gaseous products. In some embodiments, electrode insert 24 is used to introduce a lead connecting a voltage power supply and device membrane 110. Other suitable means, including conduits, openings, channels and so forth can be utilized for inserting a suitable connector for providing a net charge to the device membrane.

In the embodiments of FIGS. 7 and 8, electrode 20b is coupled to the base 18 and positioned on the opposite side of the device membrane 110 relative to electrode 20a. In some implementations the electrode 20b covers the entire bottom surface of the first channel 30. In other implementations, the electrode 20b covers portions of the bottom surface of the first channel 30. In further implementations, the electrode 20b may include a slide or other planar surface to which a conductive coating may be applied.

As further shown in FIGS. 7 and 8, the microfluidic electroporation device 10 includes a shim, such as shim 14, positioned between the upper housing 12 and the base 18. Shim 14 includes a plurality of passages for the fluid receptacle 22 and the alignment structures 16. The shim 14 may include individual shims, each of varying thicknesses, to adjust the distance between the electrode 20a and the device membrane 110. The alignment structures 16 are configured to insert into the base 18, upwards through the shim 14 and into receiving elements in the upper housing 12. The alignment structures provide mechanical support for the union of the base 18 to the upper housing 12 and enhance the structural integrity of the microfluidic electroporation device 10. A variety of alignment structure designs and elements may be utilized to secure the upper housing 12 to the base 18.

The fluid receptacle/transwell 22 includes a membrane, such as device membrane 110, designed and/or operated to trap target structures, e.g., cells, and cargo, applying principles described above.

In some implementations, the fluid receptacle/transwell 22 is positioned into the base 18 before or after shim 14 is positioned atop the base 18. The fluid receptacle/transwell 22 may be removed from the microfluidic electroporation device 10 to collect the electroporated target structures containing the cargo.

A second shim 26 is a ring shaped element that is positioned within the base 18. The fluid receptacle/transwell 22 sits atop the shim 26 and extends downward through the shim 26. The fluid receptacle/transwell 22 is placed into the base 18 after the shim 26 has been positioned on to the base. The shim 26, may include individual shims, each of varying thicknesses, to adjust the distance between the device membrane 110 and the first channel 30. The base 18 includes one or more ports 28 and can be coupled to the electrode 20b. The base 18 includes a first channel 30 (as shown in FIG. 8) that is coupled to one or more ports 28, such as ports 28a and 28b (see FIG. 8).

The base 18 may be coupled to a heatsink and/or active cooling element, for instance a Peltier device. In other arrangements, the heatsink and/or active cooling may form a bottom surface of the base 18. The heatsink and/or active cooling element can remove heat or provide active cooling as necessary to mitigate the exothermic reactions that occur during the electrophoretic movement of target structures and/or cargo as well as the electroporation process conducted in the fluid receptacle. In some implementations, the heatsink and/or active cooling element can provide cooling to further help convectively cool the electroporated cells and/or remove heat generated during the electrochemical reactions when a voltage is applied by electrodes 20.

The ports 28 are fluidically coupled to the first channel 30. The ports 28 can include an input port and an output port which are both coupled to respective opposite ends of the first channel 30. The ports 28 direct a fluid flow (generated by a pump such as pump 122 in FIG. 1) through the first channel 30. The first channel can provide an effluent path for pinning target structures (cells, for example), flow for releasing the target structures, e.g., after loading, and/or transport heat and/or electrochemical byproducts away from the system.

In some implementations, the fluid receptacle/transwell 22 includes a second channel 32 (see FIG. 8), disposed between electrode 20a and device membrane 110. The second channel can be used to apply transmembrane pressure to fluidically entrain the target structures (cells, for example) onto the membrane, and to remove payload containing target structures from the membrane (e.g., cells after genetic modification).

A method for treating cells using a microfluidic electroporation device such as that in FIGS. 7 and 8 includes: introducing cargo and cells into a fluid receptacle; positioning the target structures and cargo, preferably in close proximity, and/or contact with one another against a surface of a device membrane; permeabilizing, e.g., by electroporation or another suitable technique the positioned target structures; and collecting the electroporated target structures containing cargo, by removing the fluid receptacle, for instance. These process steps or stages can be carried out with other target structures (exosomes, other vesicles, micelles, and so forth).

Cargo is introduced into the fluid receptacle, using, for example, a micropipette. Similarly, cells or other target structures, such as exosomes, can be introduced into the fluid receptacle 22 via a micropipette. The cells can be non-adherent cells. The cells and cargo introduced into the fluid receptacle 22 may vary based on the diagnostic or therapeutic procedure being performed using the microfluidic electroporation device 10 (FIGS. 7 and 8) or system 100 (FIG. 1).

In specific embodiments, target structures and cargo are released from independent containers (e.g., target structures container 114 and cargo container 116 in FIG. 1). In one implementation, cargo is released first, followed by the release of the target structures.

The cells and cargo are positioned in close proximity and/or in contact with one another against a surface of the membrane. Initially, for example, the cells and/or the cargo may be floating in suspension within the fluid receptacle. To electroporate the cells and introduce the cargo into the electroporated cells in an efficient manner, it is helpful to position the cells in close proximity to the cargo. This is facilitated by device membrane 110 (described with reference to FIGS. 1-6, for example) which can function as a structural element to hold the cells in position so that the cargo can more readily enter the permeabilized cells.

The cells and cargo are positioned in close proximity and/or contact with one another against the surface of the membrane by techniques described above. Cargo, for example, is pinned onto a device membrane that is electrically charged, while cells or other target structures are pinned by a fluid flow. Typically, the porosity of the device membrane 110 is configured to allow fluid flow to pass through but retain the cells onto the device membrane surface.

If electrophoresis is used to enhance the transport of cargo and/or cells toward the device membrane 110, a voltage can be applied across the electrodes 20a and 20b (FIGS. 7 and 8). The electrical field applied for electrophoresis can be within the range of from about 10 to about 70V/cm, e.g., about 30-40V/cm, about 40-55V/cm, or 55-70V/cm. While the specific voltage to be applied for electrophoretic transport may vary based on the duration of applying the voltage and the dimensions of the microfluidic electroporation device 10, the electrodes 20a and 20b may be configured to generate an electrophoretic mobility of about 3 μm/second/V/cm. For example, the electrodes may be configured to generate an electrophoretic mobility of about 0.5-2, 2-5, and 5-10 μm/second/V/cm.

In implementations that use electrophoresis, the voltage used to electrophoretically enhance transport of the cargo is applied before, simultaneously, or after a voltage that is applied to electrophoretically transport the cells into a pinned position on the surface of the device membrane 110.

In some cases, a fluid flow can be provided through the first channel 30 to create a fluid pressure differential between the fluid receptacle 22 and the first channel 30 that pulls the cells and cargo down toward the membrane. The fluid flow applied to create the fluid pressure differential may be applied before, after, or simultaneously with applying a voltage to electrophoretically enhance the positioning of the cells and cargo in close proximity against the surface of the device membrane.

In one embodiment, the cells positioned on the device membrane 110 are electroporated, e.g., by applying an electric field generated between electrodes 20a and 20b, to permeabilize the cells and allow the cargo to enter the electroporated cells. The voltage applied to electroporate the positioned cells may be higher than the voltage applied during electrophoresis (in cases in which electrophoresis is used).

In some implementations, the electrodes may be configured to generate an electrical field of about 1.0 kV/cm to electroporate cells and/or about 100-300 kV/cm to electroporate exosomes. For instance, the electrodes 20a and 20b may generate an electrical field for electroporation of about 0.5 to about 500 kV/cm, about 0.5 to about 2.0 kV/cm, about 5 to about 10 kV/cm, about 10 to about 50 kV/cm, about 50 to about 100 kV/cm, or about 100 to about 500 kV/cm.

The voltage may be applied for a predetermined amount of time based on the type of target structures being electroporated. In one example, the voltage is applied for a period up to, but not exceeding 10 milliseconds as longer exposures to the applied voltage may destroy the cells.

In some situations, the voltage applied for electroporation may be applied as a series of voltage pulses or a voltage pulse train. The voltage can be applied as multiple voltage pulses that are 0.2 ms in duration, for instance. The duration of the voltage pulses that are applied to the positioned cells for electroporation may include pulse durations of about 0.001 to about 10 ms, about 10 to about 30 ms, or about 30 to about 50 ms. In some implementations, nanosecond voltage pulse durations may also be used to electroporate the positioned cells.

Based on applying the above-mentioned voltage(s), the cells positioned on the membrane may be permeabilized and the cargo may enter the cells.

Alternatively, or in addition, the cells may be permeabilized by a fixed chemically charged surface. For example, it has been suggested that polyethyleneimine can disrupt cellular membranes (I. M. Helander, H. L. Alakomi, K. Latva-Kala, P. Koski, *Polyethyleneimine is an effective permeabilizer of gram-negative bacteria*, Microbiology 143:3193-3199. Oct; 143 (Pt 10):3193-9. (1997)). Thus, by creating a positive charge on the membrane using an adsorbed polyethyleneimine layer, the cell lipid bilayer membrane may be permeabilized creating pores in the cell membrane to allow cargo, plasmids, for instance, to enter the cells. In this approach, the electroporation process can be conducted in the absence of the electric field generated by electrodes 20a and 20b. These two electrodes can still be used to set up a field for the electrophoretic transport of cargo and/or target structures, for example. In further implementations, the need for electrodes 20a and 20b is entirely bypassed. Further embodiments rely on sonoporation techniques to permeabilize the target structures.

Optionally, the cells can be convectively cooled by flowing fluid through the first channel 30 (FIGS. 7 and 8). In this way, heat, generated as a result of the electrochemical reactions needed to sustain the electrical fields applied by the electrodes 20a and 20b, may be convectively removed by the fluid flow through the first channel 30 and increase the viability of the electroporated cells now containing cargo.

Cargo-containing electroporated cells can be collected by removing the fluid receptacle. For example, after sufficiently electroporating the cells positioned on the membrane to allow the cargo to enter the cells, the cells may be collected by removing the fluid receptacle 22 from the microfluidic electroporation device 10 and using a micropipette, for instance.

After removing the cells containing cargo from the fluid receptacle 22 further analyses or processing of the cells may occur depending on the particular diagnostic or therapeutic procedure being performed.

The system and/or process described herein can employ a computing system (e.g., controller 124 in FIG. 1) that includes at least one processor for performing actions in accordance with instructions and one or more memory devices for storing instructions and data. The processor(s) can be configured to communicate, e.g., via a bus, with at least one network interface controller with one or more network interface cards connecting to one or more network devices, memory, and any other devices, an I/O interface, for example. The network interface card may have one or more network interface driver ports to communicate with the connected devices or components. Generally, the processor will execute instructions received from memory. In one illustration, the processor incorporates, or is directly connected to, a cache memory. Further details regarding a computer system that can be employed with a microfluidic electroporation device such as shown in FIGS. 7 and 8 are provided in U.S. patent application Ser. No. 15/851,393.

Figure 9:
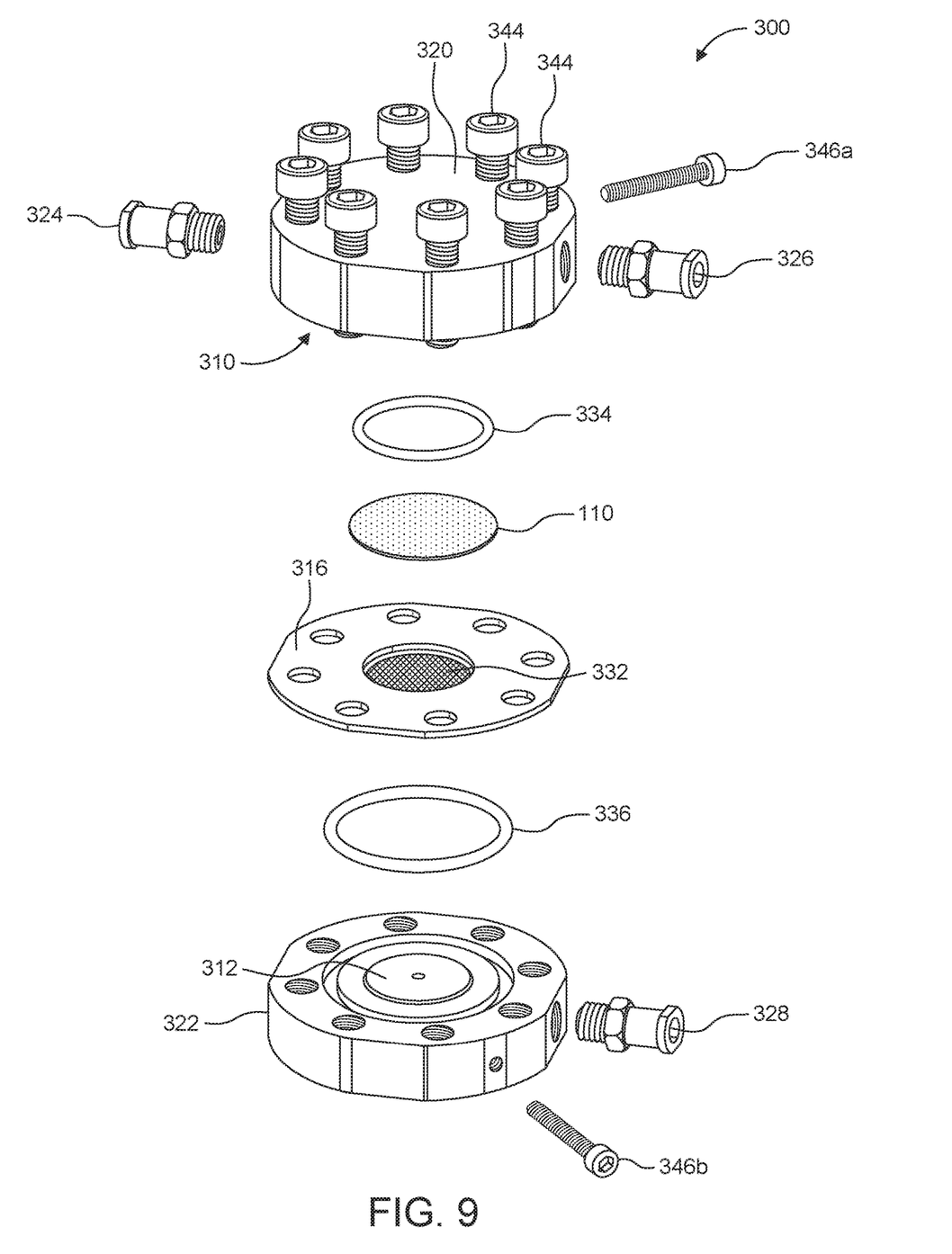
FIG. 9 is a scale exploded of the parts making up a device according to some embodiments.
Figure 10A:
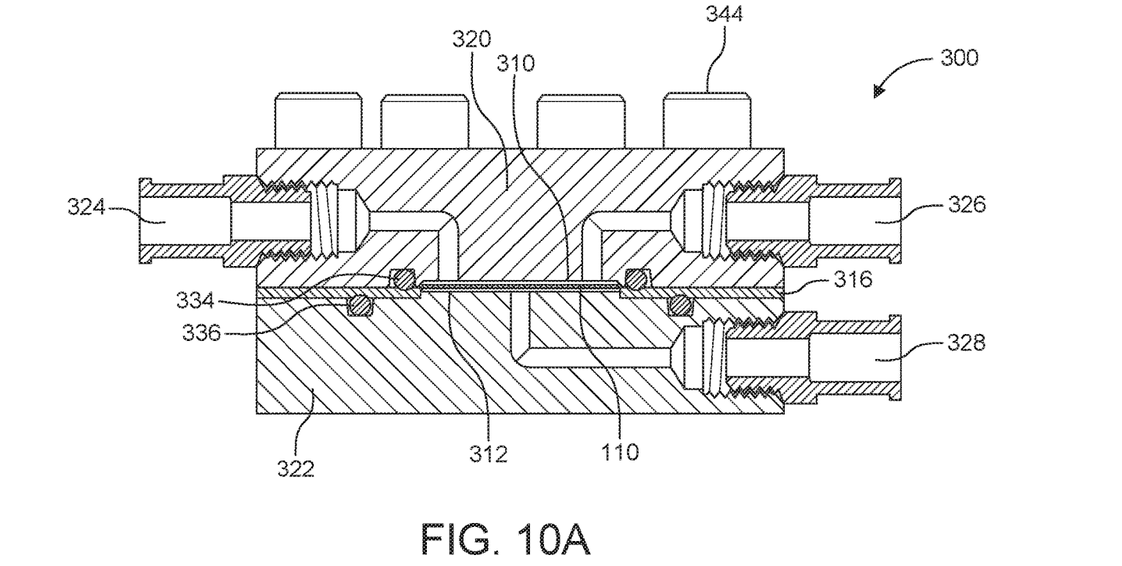
FIG. 10A is a cross-sectional side scale view and FIG. 10B is an exploded scale view of the device of FIG. 9. These views show how fluidic connections can be made and indicate illustrative dimensions for critical features.
Figure 10B:
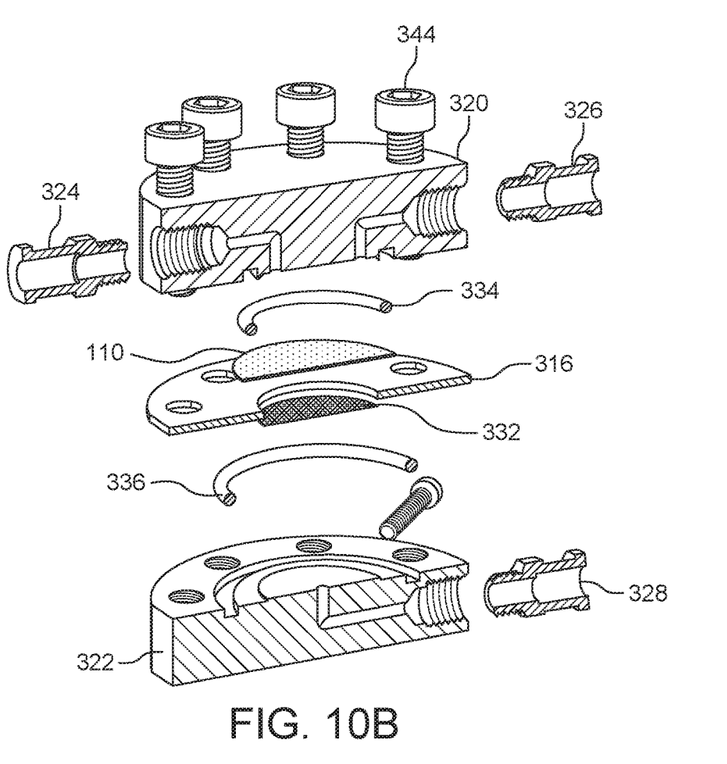

FIGS. 9, 10A and 10B illustrate another apparatus that can employ a device membrane such as described herein. FIG. 9, for example, is a perspective scale exploded view of device 300, which can be a dual-purpose viral transduction and electroporation device, as described in U.S. Provisional Application No. 62/645,277, filed on Mar. 20, 2018, incorporated herein in its entirety by this reference.

Device 300 includes two housing plates, 320 and 322, that are bolted together using, for example, #10-32 nylon screws 344. Plates 320 and 322 are made from an electrically conductive material such as, for instance, stainless steel. In the electroporation mode, the housing plates act as top and bottom electrodes, with screws 346a and 346b, made, e.g., from stainless steel, providing the electrical connection to top electrode 340a and bottom electrode 340b, respectively.

Alternatively, the housing may be comprised of a hard polymer, such as an acrylic (e.g., poly methyl methacrylate), and metal (e.g., platinum) thin film electrodes may be deposited on the floors of each chamber. Preferably, the material comprising the housing or thin film electrodes is non-reactive electrochemically when passing Faradaic current. Other implementations use an electroactive polymer such as PEDOT to pass Faradaic current while minimizing electrolysis by-products.

Each plate has a groove for O-ring style gasket 334 and 336 which provide a liquid-tight seal between each plate and spacer 316.

Spacer 316, fabricated (in part of entirely) from polytetrafluoroethylene (PTFE) or another suitable material, can range in thickness from about 0.5 millimeters (mm) to 10 mm. It separates the two plates 320, 322, and provides support for the device membrane 110. In some implementations, a mesh element 332 is employed for (added) for structural support. It can be disposed at the central region of spacer 316. The mesh 332 can be a metal or nylon mesh, glass fiber, cellulose filter, or a porous conducting polymer layer such as polyacrylamide. Typically, the mesh has large perforations relative to the size of the target structures (cells, for instance), which can pass through.

The inlet port 324 and the outlet port 326, provided e.g., by Luer Lok ports, are threaded into the body of the upper plate 320. In a similar vein, outlet port 328 is threaded into the bottom plate 322.

FIG. 10A shows a cross-sectional view of the device 300. It further shows a series of fluid flow channels formed through the body of the upper plate 320 and the bottom plate 322, for providing a fluid manifold for communication between the ports 324, 326, and 328 and the upper chamber 310 and the lower chamber 312. Additional details are provided in the cross-sectional exploded view of FIG. 3B.

During operation cargo and target structures are pinned on device membrane 110 using techniques such as described above. In specific embodiments, electrically charged cargo is positioned at device membrane 110, using, e.g., a device membrane having an opposite electrical charge. The target structures are permeabilized, by electroporation (via electrodes 320 and 322, for example) and cargo is loaded into the target structures.

Aspects of the invention can be practiced in systems for transfecting cells, that is, genetically modifying cells for use in the treatment of a mammal with a disease, condition or injury in need of treatment thereof. One example pertains to the treatment of a human in need thereof using modified acceptor cells produced by the methods described herein. Diseases encompassed by the methods described herein include, for example, heart disease, cancer, lung disease, liver disease, multiple sclerosis, hemophilia, Parkinson's disease, glaucoma and kidney disease. Of particular interest here are genetic diseases, such as cystic fibrosis or lipid storage diseases. Conditions encompassed by the present invention include, for example, diabetes or graft-versus-host disease. Treatments using modified acceptor cells as described herein include their use in treating injuries such as spinal cord injuries, chronic wounds or an ischemic injury such as stroke. Further use of the modified acceptor cells produced by the methods described herein encompass the administration/delivery of therapeutic agents to a mammal, such as, for example, drugs, vaccines, chemokines or other biological components or organic molecules. The methods described herein can be used for controlled delivery of any type of charged biomolecules to acceptor cells, including, for example, sensors to report biological phenomena within the mammalian body, or as living delivery systems. A therapeutic dose of the agent is a dose sufficient to produce a desired therapeutic effect in the subject/mammal/human. That is, a therapeutic dose is sufficient to alleviate, partially or completely, a disease, condition or injury, or specific symptoms of a disease, condition or injury. Methods of determining a therapeutic dose of an agent are known to those of skill in the art, such as a physician or pharmacologist.

In specific examples, the methods described herein is used for controlled delivery of genetic material/genes by localizing cells and plasmids together on a device membrane. The methods reasonably improve control over the number of gene integrations per cell during an electroporation process. Furthermore, the use of a device membrane as described herein, that is porous to fluid flow, allows these methods to be employed with a variety of cell types, importantly including non-adherent cells, whereas previously described systems that employed electrical trapping of plasmids could only be used with adherent cells.

REFERENCES

[1] B. J. Kirby, E. F. H. Jr, Review Zeta potential of microfluidic substrates: 2. Data for polymers, (2004) 203-213. doi:10.1002/elps.200305755.
[2] V. Tandon, S. K. Bhagavatula, W. C. Nelson, B. J. Kirby, Zeta potential and electroosmotic mobility in microfluidic devices fabricated from hydrophobic polymers: 1. The origins of charge., Electrophoresis. 29 (2008) 1092-1101. www.ncbi.nlm.nih.gov/pubmed/18306184.
[3] L. Chang, L. Li, J. Shi, Y. Sheng, W. Lu, D. Gallego-Perez, L. J. Lee, Micro-/Nano-scale Electroporation, Lab Chip. (2016) 4047-4062. doi:10.1039/C6LC00840B.
[4] T. Geng, C. Lu, Microfluidic electroporation for cellular analysis and delivery., Lab Chip. 13 (2013) 3803-21. doi:10.1039/c3lc50566a.
[5] A. Adamo, A. Arione, A. Sharei, K. F. Jensen, Flow-through comb electroporation device for delivery of macromolecules, Anal. Chem. 85 (2013) 1637-1641. doi: 10.1021/ac302887a.
[6] L. Chang, D. Gallego-Perez, X. Zhao, P. Bertani, Z. Yang, C. -L, Chiang, V. Malkoc, J. Shi, C. K. Sen, L. Odonnell, J. Yu, W. Lu, L. J. Lee, Dielectrophoresis-assisted 3D nanoelectroporation for non-viral cell transfection in adoptive immunotherapy, Lab Chip. 15 (2015) 3147-3153. doi:10.1039/c5lc00553a.
[7] T. Zhu, C. Luo, J. Huang, C. Xiong, Q. Ouyang, J. Fang, Electroporation based on hydrodynamic focusing of microfluidics with low dc voltage, Biomed. Microdevices. 12 (2010) 35-40. doi:10.1007/s10544-009-9355-z.
[8] J. Dai, T. Ito, L. Sun, R. M. Crooks, Electrokinetic Trapping and Concentration Enrichment of DNA in a Microfluidic Channel, J. Am. Chem. Soc. 125 (2003) 13026-13027.
[9] Y. Lin, M. Li, C. Wu, Simulation and experimental demonstration of the electric field assisted electroporation microchip for in vitro gene delivery enhancement, (2004) 104-108.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of controlled intracellular delivery of electrically charged biomolecules to target structures comprising:
  embossing concavities into a surface of a device membrane;
  providing electrically charged biomolecules to the device membrane;
  positioning the electrically charged biomolecules at a surface of the device membrane by providing the device membrane with an electrical charge opposite to the electrically charged biomolecules;
  directing the target structures to the surface of the device membrane by a fluid flow through the device membrane, which prevents passage of the target structures;
  organizing the target structures on the device membrane using the concavities;

then releasing the electrically charged biomolecules from the surface of the device membrane by changing an electrical charge of the device membrane;

permeabilizing the target structures; and delivering or allowing the electrically charged biomolecules to be delivered to the target structures.

2. The method of claim 1, wherein the target structures are permeabilized by electroporation, sonoporation or by using the device membrane itself.

3. The method of claim 1, wherein the electrically charged biomolecules are selected from the group consisting of plasmids, DNA and RNA and wherein the target structures are selected from the group consisting of cells, exosomes, liposomes and micelles.

4. The method of claim 1, wherein the target structures are non-adherent cells.

5. The method of claim 1, wherein the fluid flow pins the target structures to the device membrane thereby aggregating the target structures onto the device membrane in proximity to the charged biomolecules.

6. A genetic modification process comprising:

embossing concavities into a surface of a device membrane;

providing electrically charged biomolecules to the device membrane;

positioning electrically charged biomolecules at a surface of the device membrane by providing the device membrane with an electrical charge opposite to the electrically charged biomolecules;

directing target structures to the surface of the device membrane by a fluid flow and organizing the target structures on the device membrane using the concavities; and then releasing the electrically charged biomolecules from the surface of the device membrane by changing an electrical charge of the device membrane and permeabilizing the target structures to deliver biomolecules to the target structures.

7. The process of claim 6, wherein the target structures are permeabilized by electroporation, sonoporation or by using the device membrane itself.

8. The process of claim 6, wherein the biomolecules are a charged material selected from the group consisting of plasmids, DNA and RNA and wherein the target structures are selected from the group consisting of cells, exosomes, liposomes and micelles.

9. The process of claim 6, wherein the target structures are non-adherent cells.

* * * * *